US00PP09686P

United States Patent [19]

Vletter

[11] Patent Number: Plant 9,686

[45] Date of Patent: Nov. 5, 1996

[54] ANTHURIUM PLANT NAMED 'LIPSTICK'

[75] Inventor: Marinus Vletter, Waddinxveen, Netherlands

[73] Assignee: Handelskwekerij Van Der Velden B.V., Sint-Oedenrode, Netherlands

[21] Appl. No.: 509,896

[22] Filed: Aug. 1, 1995

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 9,355 10/1995 Henny ..... Plt./88.1

*Primary Examiner*—James R. Feyrer

*Attorney, Agent, or Firm*—Burns, Doane, Swecker & Mathis, L.L.P.

[57] ABSTRACT

A new distinct variety *Anthurium andraceanum* is provided which forms attractive medium to large bright lilac-pink blossoms. The growth habit is compact and well-branched. The leaves are bright green and medium in size. The coloration of the spadix closely approximates that of the spathe when the flowers are mature. The fully mature flowers turn to a darker shade of red inthe substantial absence of browning thereby extending the duration of their attractiveness while remaining on the plant. The new variety propagates well by tissue culture and is amenable to shipment without undue damage. The new variety serves well as an attractive ornamental pot plant and has been named the 'Lipstick' variety.

2 Drawing Sheets

SUMMARY OF THE INVENTION

The new variety of *Anthurium andraeanum* was created as a seedling by artificial pollination wherein parent plants were crossed which previously had been selected in the hope that they would contribute to the desired characteristics. The plant breeding was carried out in a greenhouse at Waddinxveen, Holland. It was the goal of the breeding program that resulted in the creation of the new variety to form a compact plant that was amenable to handling and shipment without undue breakage having an abundant formation of attractive long-lasting flowers of a good size, a propensity for rapid growth, a good branching habit, strong root formation, attractive dark green leaves, a good shelf life, and the ability to readily undergo propagation on a commercial scale. The parent plants utilized during the cross were among a group of largely unnamed proprietary *Anthurium andraceanum* plants that had been set aside for use as possible parent plants during the breeding program that resulted in the creation of the new variety. Any further identification of the specific parent plants that were crossed when forming the new variety of the present invention is not possible since detailed records concerning specific crosses, such as that which resulted in the new variety, are not available.

When the plants resulting from the many crosses of the breeding program were obseved, a distinctive new *Anthurium andraeanum* plant was observed and selected that possessed the following combination of characteristics:

(a) exhibits a rapid growing and compact well-balanced growth habit with strong branching,
(b) forms in abundance attractive medium to large bright lilac-pink blossoms wherein the coloration of the spadix closely approximates that of the spathe when the blossoms mature,
(c) forms attractive bright green medium-sized leaves,
(d) forms strong roots, and
(e) propagates well by the use of tissue culture.

The new variety of the present invention was found to be particularly noteworthy in that the fully mature bright lilac-pink blossoms tend to darken in coloration with age in the substantial absence of browning. Therefore such mature blossoms need not be promptly removed from the plant upon maturity and can remain upon the plant for a longer period to time while continuing to display an attractive appearance.

Approximately 3 to 4 months after potting the first flower commonly arises from the mainshoot of the new variety. The axillary shoots commonly bloom thereafter from the first expanded leaf. After 8 to 9 months a typical plant of the new variety commonly displays 1 to 2 older flowers, 3 to 4 mature flowers, and at least 2 to 4 young unrolled leaves. Finished plants when marketed at an age of 35 to 40 weeks commonly have at least 3 mature flowers of good lilac-pink coloration, several older spathes that are somewhat darker in coloration, and some immature spathes.

The new variety well meets the needs of the horticultural industry as an attractive pot plant. Good packing and shipping characteristics are exhibited by the new variety.

The new variety has not been observed under all possible environmental conditions to date. Accordingly, it is possible that the phenotype may vary somewhat with variations in the environment, such as changes in temperature, light level, and fertilization.

When the new variety of the present invention is compared to the 'Avanti' variety (non-patented in the United States), the new variety is found to display a more compact growth habit, and to form a more strongly branched plant.

The new variety of the present invention has been found to readily undergo asexual propagation in Holland by the use of tissue culture and division. Such asexual reproduction as performed in Holland has shown that the characteristics of the new variety are homogeneous and stable and are strictly transmissible from one generation to another.

The new variety has been named 'Lipstick' and is being marketed under the ANDES trademark.

BRIEF DESCRIPTION OF THE PHOTOGRAPHS

The accompanying photographs show as nearly true as it is reasonably possible to make the same, in a color illustration of this character, the new variety while growing in a greenhouse at Waddinxveen, Holland during June 1995. The plant was reproduced by tissue culture and is shown while approximately 38 weeks of age and growing in a 20 cm. pot.

DETAILED DESCRIPTION

Figure 1:
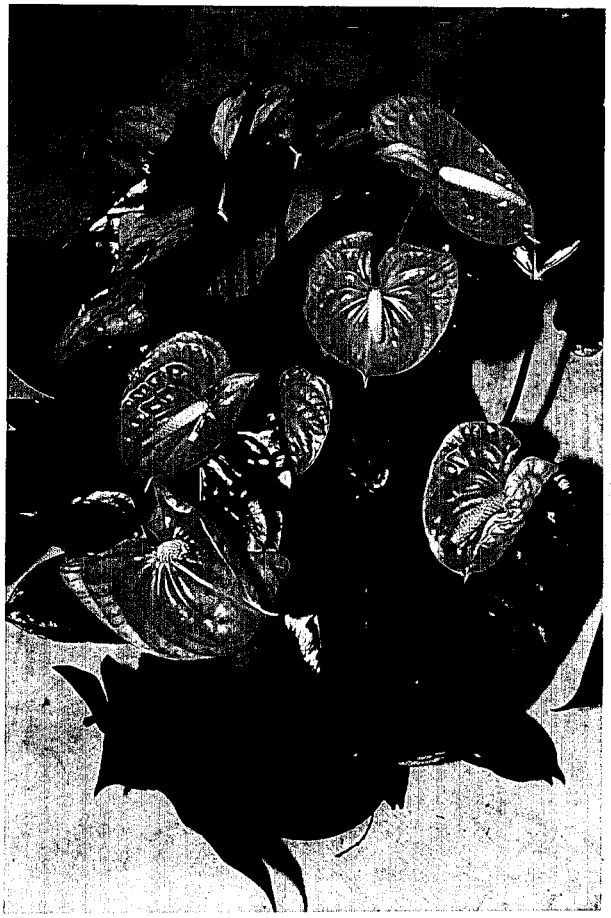
FIG. 1 illustrates an overall plant of the new variety wherein the compact growth habit, attractive bright lilac-pink blossoms, and bright green foliage are apparent.
Figure 2:
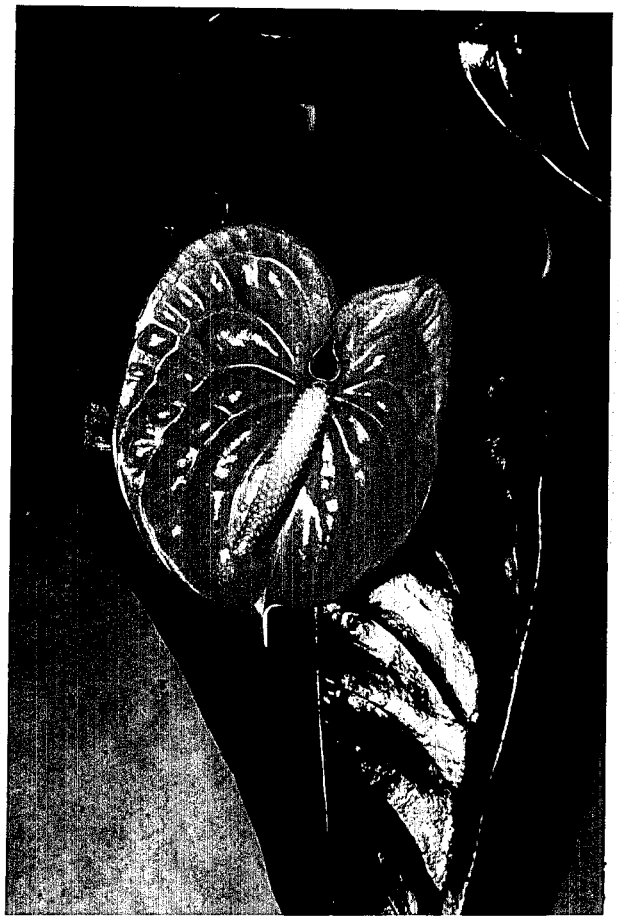
FIG. 2 illustrates a closer view of a typical flower and leaf of the new variety. In view of the stage of flower maturity only the distal end of the spadix has assumed a coloration that approximates that of the spathe.

The following description of the new variety of *Anthurium andraeanum* is based upon the observation of plants growing under greenhouse conditions primarily at Wageningen, Holland. The chart used in the identification of colors is that of The Royal Horticultural Society (R.H.S. Colour Chart) of London, England. Color terminology in common terms sometimes is included as an aid to the reader. The plants were being grown in 20 cm. pots and were approximately 35 to 40 weeks of age.

Botanical classification: *Anthurium andraeanum,* cv. 'Lipstick'.

Parentage: Unidentifiable parent plants of *Anthurium andraeanum.*

Plant:

*Height.*—Medium to large, when mature approximately 60 to 80 cm. in height and approximately 50 to 65 cm. in width when grown in a 20 cm. pot at the end of 35 to 40 weeks. There is some correlation between the pot size and the size of the plant. For instance, when grown in a 27 cm. pot, a plant height of 80 to 100 cm. commonly can be produced.

*Form.*—Compact and well-balanced.

Branches:

*Character.*—Strong.

*Color.*—Mixture of red and green (as illustrated).

Leaves:

*Leaf size.*—Medium. Mature leaves commonly are approximately 23 to 26 cm. in length on average, and approximately 15 to 17 cm. in width on average.

*Blade shape.*—Ovate and heart-shaped.

*Position of lobes.*—Free.

*Leaf blade tip.*—Acute.

*Color.*—Upper surface: Medium to dark green, commonly ranges from Green Group 135A to 139A. Under surface: Yellow-Green Group 146B.

*Petiole length.*—Medium.

*Petiole color.*—Medium green on mature leaves and red-brown on young leaves.

Inflorescence:

*Number of lowers.*—Commonly one flower forms per each leaf.

*Peduncle length.*—Medium.

*Cross section of peduncle.*—Elliptic.

*Peduncle size.*—Thick.

*Peduncle color.*—Light green with some reddish coloration.

*Spathe shape.*—Broad ovate.

*Position of spathe lobes.*—Free.

*Spathe tip.*—Rounded.

*Spathe top.*—Acuminate.

*Spathe size.*—Medium to large, commonly approximately 13 to 14 cm in length and approximately 11 to 12 cm in width.

*Spathe glossiness.*—Medium.

*Spathe blistering.*—Strong.

*Spathe depth of sinus.*—Deep.

*Spathe cross section at distal end.*—Concave.

*Spathe angle of distal end to peduncle.*—Substantially at a right angle.

*Spathe distance between spadix and sinus.*—Very short to short.

*Spathe color.*—Upper side: bright lilac-pink, Red Group 52A but somewhat redder. Under side: bright lilac-pink, Red Group 52A but somewhat redder, with no substantial vein color contrast.

*Spadix length.*—Medium, commonly approximately 6 to 7 cm. in length.

*Spadix width.*—Medium, approximately 10 to 11 mm.

*Spadix cross section at middle.*—Elliptic.

*Spadix longitudinal configuration.*—Substantially straight (as illustrated).

*Spadix taper towards tip.*—Medium.

*Spadix color.*—Main body: Red Group 53D to Greyed-Purple Group 184D. Lighter and darker shades commonly are present in the same hue. Tip: Red Group 44A.

*Pollen coloration.*—White to cream-white.

*Pistils.*—Commonly lighter than Red Group 53D, and commonly protrude between and extend beyond the staminate flowers to a distance of approximately 0.5 to 1 mm.

I claim:

1. A new and distinct variety of *Anthurium andraeanum* plant characterized by the following combination of characteristics:

(a) exhibits a rapid growing and compact well-balanced growth habit with strong branching,
(b) forms in abundance attractive medium to large bright lilac-pink blossoms wherein the coloration of the spadix closely approximates that of the spathe when the blossoms mature,
(c) forms attractive bright green medium-sized leaves,
(d) forms strong roots, and
(e) propagated well by the use of tissue culture;

substantially as herein shown and described.

* * * * *